United States Patent
Corl et al.

(10) Patent No.: US 8,419,648 B2
(45) Date of Patent: Apr. 16, 2013

(54) ULTRA MINIATURE PRESSURE SENSOR

(75) Inventors: Paul Corl, Palo Alto, CA (US); Robert Obara, Sunnyvale, CA (US); John Ortiz, East Palo Alto, CA (US)

(73) Assignee: Volcano Corporation, San Diego, CA (US)

( * ) Notice: Subject to any disclaimer, the term of this patent is extended or adjusted under 35 U.S.C. 154(b) by 130 days.

(21) Appl. No.: 11/303,249

(22) Filed: Dec. 15, 2005

(65) Prior Publication Data

US 2006/0094982 A1 May 4, 2006

Related U.S. Application Data

(63) Continuation of application No. 10/247,043, filed on Sep. 19, 2002, now Pat. No. 6,976,965, which is a continuation of application No. 09/644,111, filed on Aug. 21, 2000, now Pat. No. 6,767,327, which is a continuation of application No. 08/912,879, filed on Aug. 15, 1997, now Pat. No. 6,106,476, which is a continuation-in-part of application No. 08/710,062, filed on Sep. 9, 1996, now Pat. No. 5,715,827, which is a continuation of application No. 08/300,445, filed on Sep. 2, 1994, now abandoned.

(51) Int. Cl.
*A61B 5/02* (2006.01)

(52) U.S. Cl.
USPC ............................................ 600/486; 600/485

(58) Field of Classification Search .................. 600/300, 600/481, 485–489, 500
See application file for complete search history.

(56) References Cited

U.S. PATENT DOCUMENTS

| | | | |
|---|---|---|---|
| 3,490,441 A | 1/1970 | Curtis | |
| 3,545,275 A | 12/1970 | Harrison | |
| 3,724,274 A | 4/1973 | Millar | |
| 3,748,623 A | 7/1973 | Millar | |
| 4,020,830 A | 5/1977 | Johnson et al. | |
| 4,274,423 A * | 6/1981 | Mizuno et al. | 600/488 |
| 4,554,927 A | 11/1985 | Fussell | |
| 4,610,256 A | 9/1986 | Wallace | |

(Continued)

FOREIGN PATENT DOCUMENTS

| | | |
|---|---|---|
| DE | 2246687 | 3/1974 |
| DE | 2708607 | 2/1977 |

(Continued)

OTHER PUBLICATIONS

Chau, Hin-Leung, "An Ultraminiature Solid-State Pressure Sensor for a Cardiovascular Catheter," Abstract of Electron Devices, IEEE Transactions, vol. 35, issue 12, Dec. 1988.

(Continued)

*Primary Examiner* — Patricia Mallari
*Assistant Examiner* — Michael D'Angelo
(74) *Attorney, Agent, or Firm* — Haynes and Boone, LLP

(57) ABSTRACT

A method of measuring blood pressure and velocity proximally and distally of a stenosis in a vessel carrying blood includes the steps of providing a guide wire having both a pressure sensor and a velocity sensor disposed on a distal region of the guide wire, introducing the guide wire into the vessel, advancing the guide wire to position the pressure sensor and the velocity sensor proximally and distally of the stenosis, and measuring the blood pressure and velocity proximally and distally of the stenosis with the pressure sensor and the velocity sensor.

75 Claims, 6 Drawing Sheets

U.S. PATENT DOCUMENTS

| | | | |
|---|---|---|---|
| 4,659,235 A * | 4/1987 | Gilmore et al. | 374/143 |
| 4,722,348 A | 2/1988 | Ligtenberg et al. | |
| 4,733,669 A | 3/1988 | Segal | |
| 4,748,986 A * | 6/1988 | Morrison et al. | 600/585 |
| 4,771,782 A | 9/1988 | Millar | |
| 4,807,477 A * | 2/1989 | Myers et al. | 73/708 |
| 4,808,164 A | 2/1989 | Hess | |
| 4,815,472 A | 3/1989 | Wise et al. | |
| 4,872,483 A * | 10/1989 | Shah | 137/557 |
| 4,881,410 A | 11/1989 | Wise et al. | |
| 4,901,735 A | 2/1990 | von Berg | |
| 4,908,693 A * | 3/1990 | Nishiguchi | 257/417 |
| 4,945,762 A * | 8/1990 | Adamic, Jr. | 73/862.622 |
| 4,953,553 A | 9/1990 | Tremulis | |
| 4,964,409 A * | 10/1990 | Tremulis | 600/434 |
| 5,013,396 A | 5/1991 | Wise et al. | |
| 5,046,497 A | 9/1991 | Millar | |
| 5,050,297 A | 9/1991 | Metzger | |
| 5,050,606 A | 9/1991 | Tremulis | |
| 5,067,491 A | 11/1991 | Taylor et al. | |
| 5,085,223 A | 2/1992 | Lars et al. | |
| 5,113,868 A * | 5/1992 | Wise et al. | 600/488 |
| 5,125,137 A | 6/1992 | Corl et al. | |
| 5,163,445 A | 11/1992 | Christian et al. | |
| 5,174,295 A | 12/1992 | Christian et al. | |
| 5,178,153 A | 1/1993 | Einzig | |
| 5,178,159 A | 1/1993 | Christian | |
| 5,207,102 A | 5/1993 | Takahashi et al. | |
| 5,207,103 A | 5/1993 | Wise et al. | |
| 5,226,421 A | 7/1993 | Frisbie et al. | |
| 5,226,423 A | 7/1993 | Tenerz et al. | |
| 5,240,437 A | 8/1993 | Christian | |
| 5,313,957 A | 5/1994 | Little | |
| 5,348,481 A | 9/1994 | Ortiz | |
| 5,358,409 A | 10/1994 | Obara | |
| 5,412,994 A | 5/1995 | Cook et al. | |
| 5,450,091 A | 9/1995 | Hama | |
| 5,450,853 A | 9/1995 | Hastings | |
| 5,517,989 A | 5/1996 | Frisbie et al. | |
| 5,551,301 A | 9/1996 | Cowan | |
| 5,668,320 A | 9/1997 | Cowan | |
| 5,715,827 A | 2/1998 | Corl et al. | |
| 5,807,477 A | 9/1998 | Hearn et al. | |
| 5,902,248 A | 5/1999 | Millar et al. | |
| 6,106,476 A | 8/2000 | Corl et al. | |
| 6,112,598 A | 9/2000 | Tenerz et al. | |
| 6,142,958 A | 11/2000 | Hammarstrom et al. | |
| 6,167,763 B1 | 1/2001 | Tenerz et al. | |
| 6,976,965 B2 | 12/2005 | Corl et al. | |
| 7,033,325 B1 | 4/2006 | Sullivan | |
| 7,097,620 B2 | 8/2006 | Corl et al. | |
| 2006/0074318 A1 | 4/2006 | Ahmed et al. | |

FOREIGN PATENT DOCUMENTS

| | | |
|---|---|---|
| EP | 0006577 | 6/1979 |
| EP | 0036171 | 3/1981 |
| EP | 0115548 | 8/1984 |
| EP | 0215528 | 9/1986 |
| EP | 0224997 | 9/1986 |
| EP | 0313836 | 5/1989 |
| EP | 0387453 | 12/1989 |
| WO | WO8103613 | 12/1981 |
| WO | WO 88/00810 | 2/1988 |
| WO | WO 90/06722 | 6/1990 |
| WO | WO 90/07906 | 7/1990 |
| WO | WO 97/00641 | 1/1997 |

OTHER PUBLICATIONS

Chau, Hin-Leung, "An Ultraminiature Solid-State Pressure Sensor for a Cardiovascular Catheter," Transducers 1987.

Ko et al., "Development of a Miniature Pressure Transducer for Biomedical Applications," (IEEE Transactions on Electron Devices, vol. ED-26 1979), 10 pages.

Non-Final Office Action issued in U.S. Appl. No. 11/650,064, mailed Jun. 4, 2010, 11 pages.

Non-Final Office Action issued in U.S. Appl. No. 10/247,043; mailed Jun. 17, 2004; 11 pages.

Non-Final Office Action issued in U.S. Appl. No. 13/169,174; mailed Jun. 20, 2012; 9 pages.

Final Office Action issued in U.S. Appl. No. 10/247,043; mailed Mar. 23, 2005; 9 pages.

Final Office Action issued in U.S. Appl. No. 10/247,043; mailed Jul. 1, 2005; 9 pages.

Non-Final Office Action issued in abandoned U.S. Appl. No. 11/442,684; mailed Oct. 3, 2007, 6 pages.

Esashi, M., et al., "Fabrication of Catheter-Tip and Sidewall Miniature Pressure Sensor," IEEE Transactions on Electron Devices, vol. ED-29, No. 1, Jan. 1982, pp. 57-63.

European Search Report, EPO, for EP Application No. 83100989.9, Publication No. 0115548, Search completed Aug. 29, 1983.

European Supplementary Search Report, EPO, for EP Application No. 95928311, Publication No. 0778746, Search completed Sep. 3, 1997.

European Search Report, EPO, for EP Application No. 06075026, Publication No. 1658808, Search completed Mar. 17, 2006.

Ji,, Jin, et al., An Ultraminiature CMOS Pressure Sensor for a Multiplexed Cardiovascular Catheter, IEEE Transactions, vol. 39, No. 10, Oct. 1992.

Wallis, George, et al., Field Assisted GlassMetal Sealing, AIP Journal of Applied Physics, Citation: J. Appl. Phys. 40, 3946 (1969); DOI: 10.1063/1/1657121.

Terry, Stephen C. et al., A Gas Chromatographic Air Analyzer Fabricated on a Silicon Wafer, IEEE Transactions, Jul. 30, 1979.

Roylance, Lynn Michelle, et al., A Batch-Fabricated Silicon Accelerometer, IEEE Transactions, vol. ED-26, No. 12, Dec. 1979.

Peterson, Kurt E., Silicon as a Mechanical Material, Proceedings of the IEEE, vol. 70, No. 5, May 1982.

Sander, Craig S., et al., A Monolithic Capacitive Pressure Sensor With Pulse-Period Output, IEEE Transactions, vol. ED-27, No. 5, May 1980.

Tufte, O.N., et al., Silicon Diffused-Element Piezoresistive Diaphragms, Journal of Applied Physics, vol. 33, No. 11, Nov. 1962.

Tufte, O.N., et al. Piezoresistive Properties of Silicon Diffused Layers, Citation: J. Appl. Phys. 24, 313 (1963); doi: 10/1063/1.1702605.

Kanda, Yozo, A Graphical Representation of the Piezoresistance Coefficients in Silicon, IEEE Transactions, vol. ED-29, No. 1, Jan. 1982.

Guckel, H. et al., Laser-Recrystallized Piezoresistive Micro-Diaphragm Sensor, IEEE Transactions, 1985.

Sridhar, Uppili, et al., Temperature Coefficient of Resistance of Piezoresistors, IEEE Transactions, 1992.

Chau, K.H.-L., et al., High-Stress and Overrange Behavior of Sealed-Cavity Polysilicon Pressure Sensors, IEEE Transactions, 1990.

Sugiyama, Susumu, et al., Surface Micromachined Micro-Diaphragm Pressure Sensors, IEEE Transactions, 1991.

Samaun, et al., An IC Piezoresistive Pressure Sensor for Biomedical Instrumentation, May 1972.

Clark, Samuel K., et al. Pressure Sensitivity in Anisotropically Etched Thin-Diaphragm Pressure Sensors, IEEE Transactions, vol. ED-26, No. 12, Dec. 1979.

Timoshenko, S., et al., Theory of Plates and Shells, McGraw-Hill Book Company, 1959.

Lee, Ki-Won, et al., SENSIM: A Simulation Program for Solid-State Pressure Sensors, IEEE Transactions, vol. ED-29, No. 1, Jan. 1982.

Maseeh, Fariborz, et al., A CAD Architecture for Microelectromechanical Systems, IEEE Transactions, 1990.

Senturia, Stephen D., et al., A Computer-Aided Design System for Microelectromechanical Systems (MEMCAD), IEEE, Journal of Microelectromechanical Systems, vol. 1, No. 1, Mar. 1992.

Zhang, Y., et al., Pressure Sensor Design and Simulation Using the Caemens-D Module, Center for Integrated Sensors and Circuits, University of Michical, IEEE Transactions, 1990.

Huang, J.C.-M., et al., A Monolithic Pressure-pH Sensor for Esophageal Studies, Departmetn of Electrical and Computer Engineering, University of Michigan, IEEE Transactions, 1982.

Lee, Yong S., et al., A Batch-Fabricated Silicon Capacitive Pressure Transducer with Low Temperature Sensitivity, IEEE Transactions, vol. ED-29, No. 1, Jan. 1982.

Chau, Hin-Leung, Scaling Limits in Batch-Fabricated Silicon Pressure Sensors, IEEE Transactions, vol. ED-34, No. 4, Apr. 1987.

\* cited by examiner

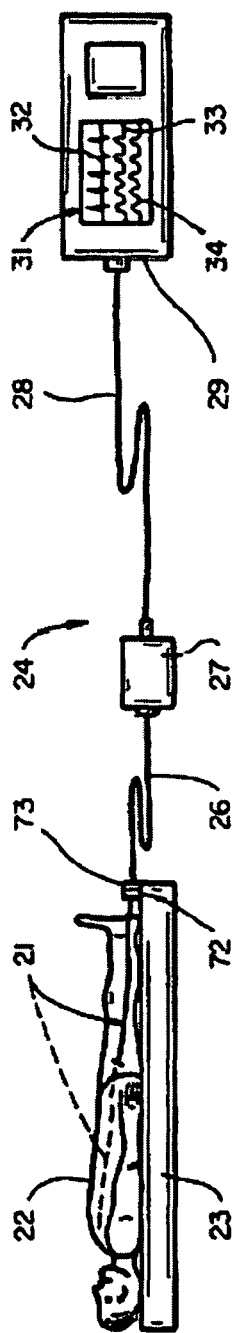
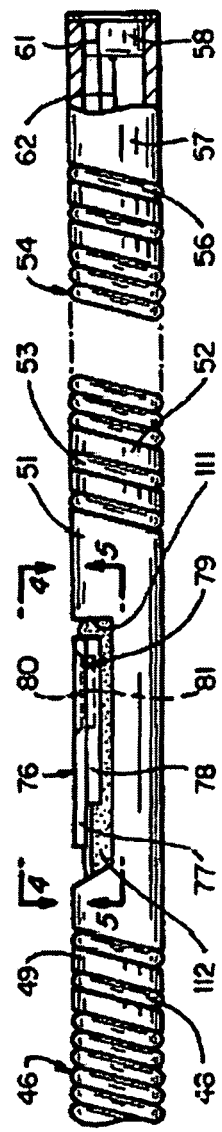
FIG_1
FIG_2
FIG_3

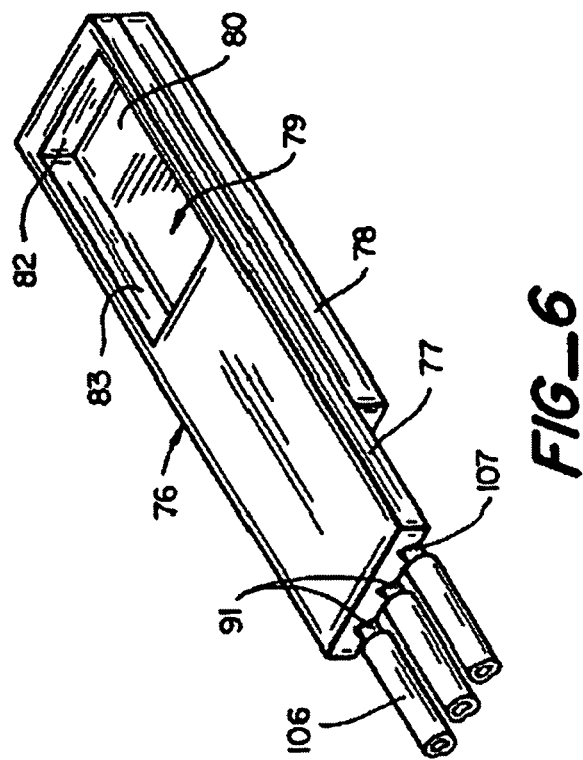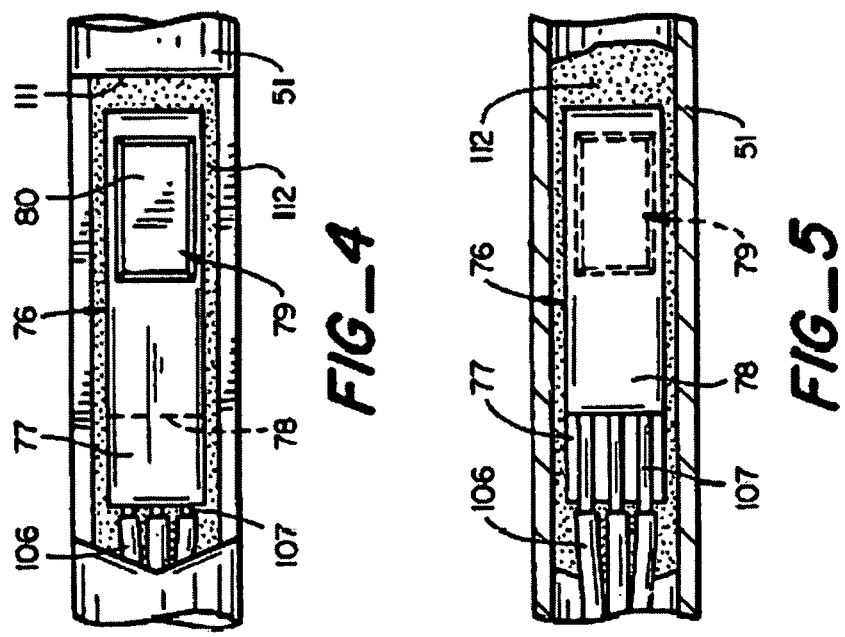

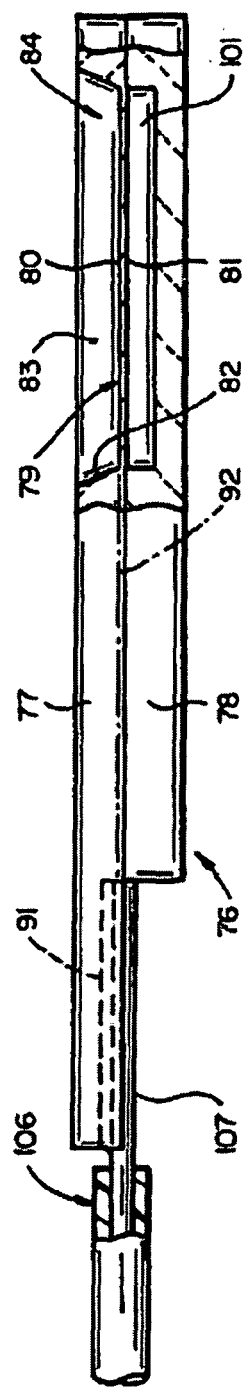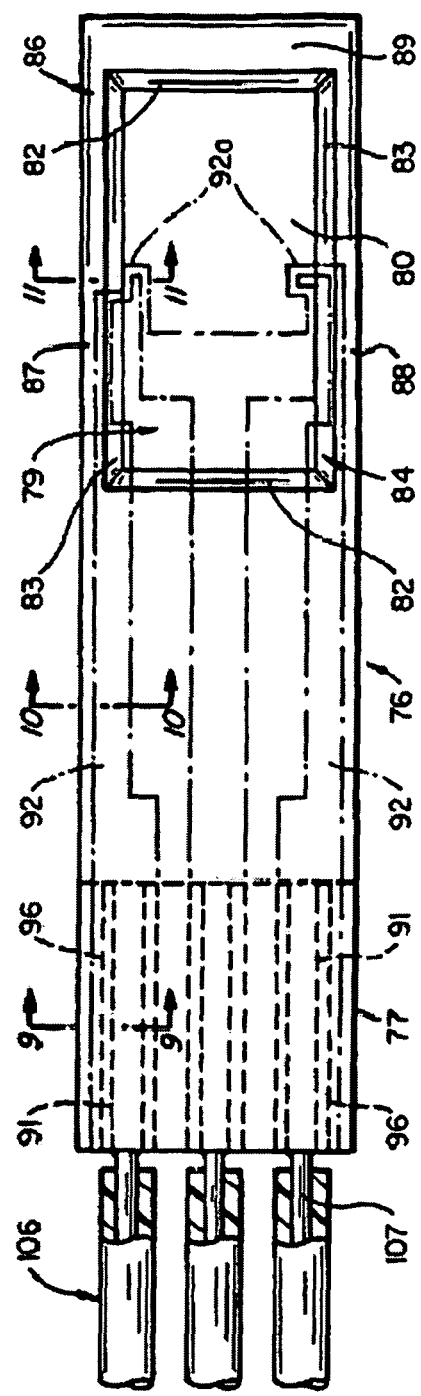

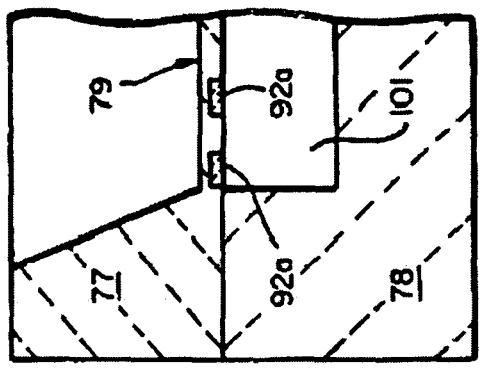
FIG_11
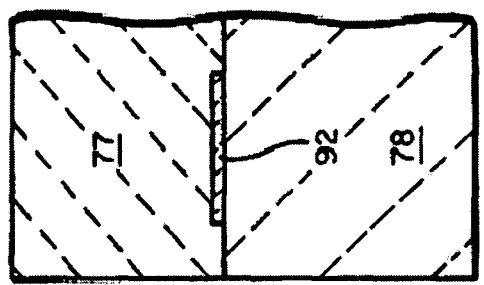
FIG_10
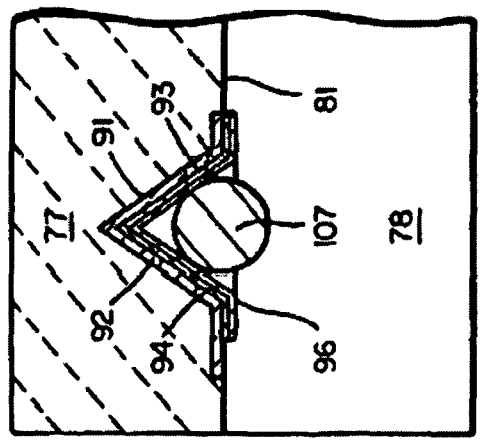
FIG_9
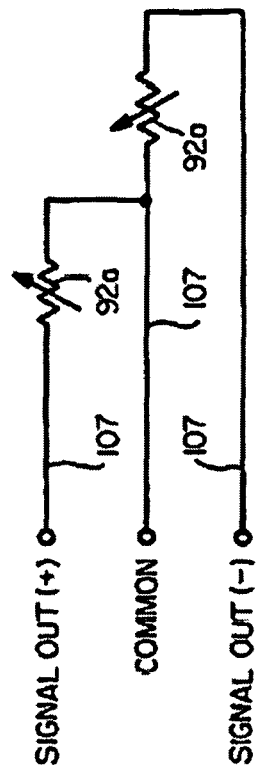
FIG_12

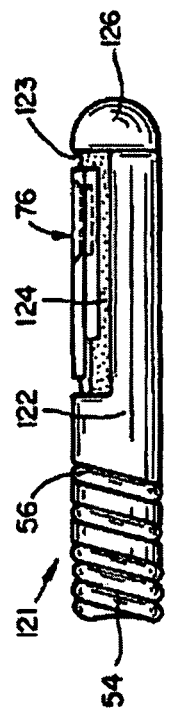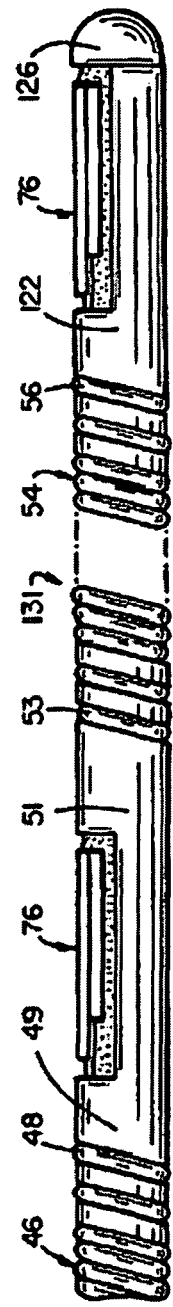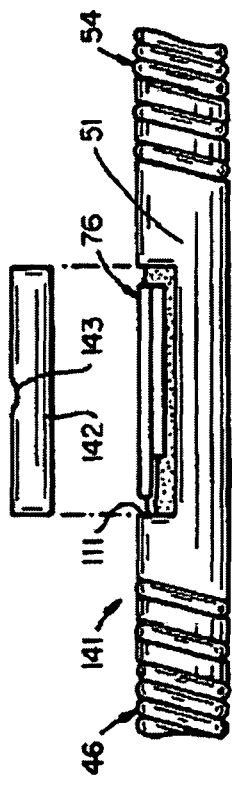

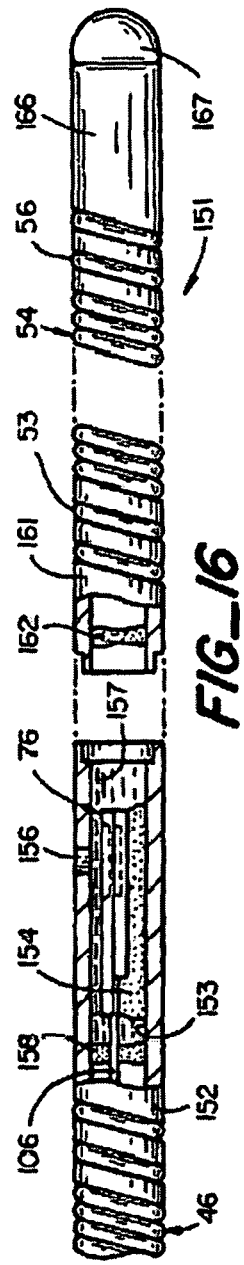
FIG_16
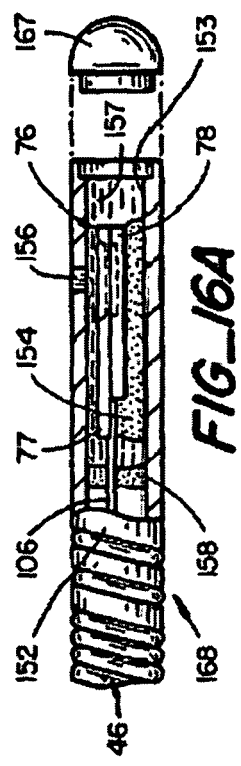
FIG_16A
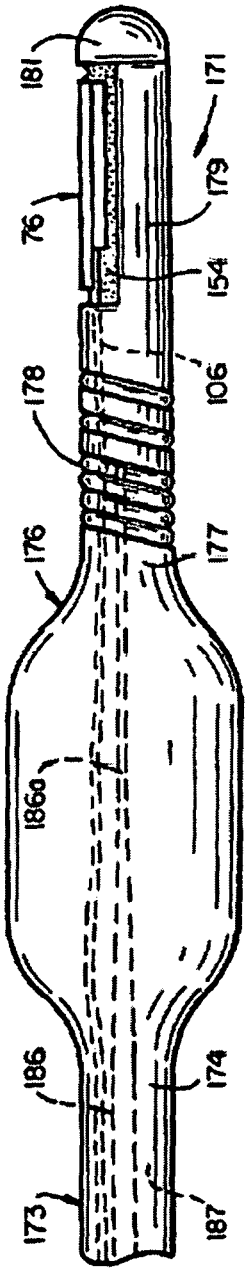
FIG_17

ULTRA MINIATURE PRESSURE SENSOR

CROSS-REFERENCE TO RELATED APPLICATION

This is a continuation of U.S. application Ser. No. 10/247,043, filed Sep. 19, 2002, now U.S. Pat. No. 6,976,965, which is a continuation of U.S. application Ser. No. 09/644,111, filed Aug. 21, 2000, now U.S. Pat. No. 6,767,327, which is a continuation of U.S. application Ser. No. 08/912,879, filed Aug. 15, 1997, now U.S. Pat. No. 6,106,476, which is a continuation-in-part of U.S. application Ser. No. 08/710,062, filed Sep. 9, 1996, now U.S. Pat. No. 5,715,827, which is a continuation of U.S. application Ser. No. 08/300,445, filed Sep. 2, 1994, now abandoned, all of which are hereby expressly incorporated by reference in their entirety.

FIELD OF THE INVENTION

This invention relates to an ultra miniature pressure sensor and guide wire and apparatus using the same and method, which is particularly suitable for making pressure measurements in coronary arteries of human beings.

It has been well known that it is desirable to make pressure measurements in vessels and particularly in coronary arteries with the advent of angioplasty. Typically in the past, such pressure measurements have been made by measuring the pressure at a proximal extremity of a lumen provided in a catheter advanced into the coronary artery of interest. However, such an approach has been less efficacious as the diameters of the catheters became smaller with the need to advance the catheter into smaller vessels. This made necessary the use of smaller lumens which gave less accurate pressure measurements and in the smallest catheters necessitated the elimination of such a pressure lumen entirely. In an attempt to overcome these difficulties, ultra miniature pressure sensors have been proposed for use on the distal extremities of catheters. However, it has not been feasible prior to the present invention to provide such ultra miniature pressure sensors which are capable of being incorporated in a guide wire for making pressure measurements in a very small arterial vessels. There is therefore a need for a new and improved ultra miniature pressure sensor and a guide wire and apparatus utilizing the same.

In general it is an object of the present invention to provide an ultra miniature pressure sensor and guide wire and apparatus utilizing the same making possible pressure and velocity measurements.

Another object of the invention is to provide a sensor which can be utilized on the distal extremity of a guide wire 0.018" or 0.014" in diameter.

Another object of the invention is to provide a sensor of the above character which is formed of a silicon chip of a small dimension which is reinforced by an additional member to provide reinforcement for the chip.

Another object of the invention is to provide a sensor of the above character in which a thin diaphragm is formed in the crystalline silicon chip.

Another object of the invention is to provide a sensor of the above character in which the reinforcing member extends for approximately 200 microns beyond the silicon diaphragm.

Another object of the invention is to provide a guide wire with the above character in which the number of conducting wires required is kept to a minimum.

Another object of the invention is to provide a guide wire and method in which simultaneous pressure and velocity measurements can be made.

Another object of the invention is to provide a guide wire of the above character in which the diaphragm area has been maximized.

Another object of the invention is to provide a guide wire with the above character in which two pressure sensors are provided on the guide wire which are spaced apart so that pressure measurements can be made on both sides of a stenosis.

Another object of the invention is to provide a guide wire of the above character in which the sensors are covered to prevent the formation of blood clots.

Another object of the invention is to provide an apparatus of the above character which includes a guide wire with an integral inflatable balloon.

Another object of the invention is to provide an apparatus of the above character in which temperature compensation can be provided.

Another object of the invention is to provide an apparatus of the above character which can be utilized in a half-bridge configuration.

Additional features and objects of the invention will appear from the following description in which the preferred embodiments are set forth in detail in conjunction with the accompanying drawings.

BRIEF DESCRIPTION OF THE DRAWINGS

FIG. 1 is a schematic illustration showing use of a guide wire incorporating a pressure sensor of the present invention and apparatus utilizing the same in conjunction with a patient undergoing a catheterization procedure for diagnosis or treatment.

FIG. 2 is a side elevational view of a guide wire incorporating an ultra miniature pressure sensor of the present invention.

FIG. 3 is an enlarged side elevational view of the distal extremity of the guide wire shown in FIG. 2 and showing the pressure sensor mounted therein.

FIG. 4 is a top plan view looking along the line 4-4 of FIG. 3.

FIG. 5 is a bottom plan view looking along the line 5-5 of FIG. 3.

FIG. 6 is an isometric view of the pressure sensor shown in FIGS. 3, 4 and 5 with the lead wires connected thereto.

FIG. 7 is a side elevational view of the pressure sensor shown in FIG. 6.

FIG. 8 is a top plan view of the pressure sensor shown in FIGS. 6 and 7.

FIG. 9 is a cross-sectional view taken along the line 9-9 of FIG. 8.

FIG. 10 is a cross-sectional view taken along the line 10-10 of FIG. 8.

FIG. 11 is a cross-sectional view taken along the line 11-11 of FIG. 8.

FIG. 12, is a schematic diagram of the circuitry utilized in the pressure sensor shown in FIGS. 6-11.

FIG. 13 is a side elevational view of the distal extremity of another guide wire incorporating the pressure sensor with the sensor of the present invention being mounted in the tip housing.

FIG. 14 is a side elevational view of the distal extremity of a guide wire having first and second pressure sensors mounted in the distal extremity of the same spaced apart to permit simultaneous measurements of proximal and distal pressures with respect to a stenosis.

FIG. 15 is a partial side elevational view of another guide wire incorporating the present invention with an enclosed pressure sensor.

FIG. 16 is a side elevational view partially in section of the distal extremity of another guide wire incorporating the present invention in which the pressure sensor is enclosed in a transition housing.

FIG. 16A is a side elevational view in section showing an end-mounted pressure sensor incorporating the present invention.

FIG. 17 is a side elevational view in section of a guide wire housing a tip-mounted sensor incorporating the present invention with an integral balloon.

DETAILED DESCRIPTION OF THE INVENTION

In general, the guide wire of the present invention having pressure sensing capabilities is comprised of a flexible elongate element having proximal and distal extremities and having a diameter of 0.018" and less. The pressure sensor is mounted on the distal extremity of a flexible elongate element. It is comprised of a crystal semiconductor material having a recess therein and forming a diaphragm bordered by a rim. A reinforcing member is bonded to the crystal and reinforces the rim of the crystal and has a cavity therein underlying the diaphragm and exposed to the diaphragm. A resistor having opposite ends is carried by the crystal and has a portion thereof overlying a portion of the diaphragm. Leads are connected to opposite ends of the resistor and extend within the flexible elongate member to the proximal extremity of the flexible elongate member.

More in particular, the guide wire 21 of the present invention having pressure measuring capabilities as shown in FIG. 1 is one that is adapted to be used in connection with a patient 22 lying on a table or a bed 23 in a cath lab of a typical hospital in which a catheterization procedure such as for diagnosis or treatment is being performed on the patient. The guide wire 21 is used with apparatus 24 which consists of a cable 26 which connects the guide wire 21 to an interface box 27. Interface box 27 is connected by another cable 28 to a control console 29 which has incorporated as a part thereof a video screen 31 on which a waveform 32 displaying ECG measurements may be provided as well as two traces 33 and 34 displaying pressure measurements being made by the guide wire 21.

The guide wire 21 is shown more in detail in FIG. 2 and as shown therein, the guide wire 21 can be constructed utilizing the various constructions as shown in U.S. Pat. Nos. 5,125,137; 5,163,445; 5,174,295; 5,178,159; 5,226,421; and 5,240,437. As disclosed therein, such a guide wire consists of a flexible elongate element 41 having a proximal and distal extremities 42 and 43 and which can be formed of a suitable material such as stainless steel having an outside diameter for example of 0.018" or less and having a suitable wall thickness as for example, 0.001" to 0.002" and conventionally called a "hypotube" having a length of 150-170 centimeters. Where a smaller guide wire is desired, the hypotube 41 can have an exterior diameter of 0.014" or less. Typically such a guide wire includes a core wire (not shown) of the type disclosed in the above identified patents which extends from the proximal extremity to the distal extremity of the flexible elongate element 41 to provide the desired torsional properties for guide wires (See U.S. Pat. No. 5,163,445, col. 18:40-51) to facilitate steering of the guide wire 21 in the vessel.

A coil spring 46 is provided and is formed of a suitable material such as stainless steel. It has an outside diameter of 0.018" and is formed from a wire having a diameter of 0.003".

The spring 46 is provided with a proximal extremity 47 which is threaded onto the distal extremity 43 of the flexible elongate member 41. The distal extremity 48 of the coil spring 46 is threaded onto the proximal extremity 49 of an intermediate or transition housing 51 such as disclosed in U.S. Pat. No. 5,174,295, formed of a suitable material such as stainless steel having an outside diameter of 0.018" and having a suitable wall thickness as for example, 0.001" to 0.002". The housing 51 is provided with a distal extremity 52 which has the proximal extremity 53 of a coil spring 54 threaded thereon. The coil spring 54 is formed of a highly radiopaque material such as palladium or a tungsten platinum alloy. The coil spring 46 can have a suitable length as for example 27 centimeters whereas, the coil spring 54 can have a suitable length such as 3 centimeters. The intermediate or transition housing 51 can have a suitable length as for example, one to five millimeters. The use of the two coils 46 and 54 on opposite ends of the housing 61 provides a very flexible floppy tip for the guide wire 21 as described in U.S. Pat. No. 5,174,295. The coil 54 is provided with a distal extremity which is threaded onto an end cap 57 also formed of a suitable material such as stainless steel and having an outside diameter of 0.018" and a wall thickness of 0.001" to 0.002". An ultrasonic transducer 58 is mounted in the end cap in a manner described in U.S. Pat. No. 5,125,137 and has conductors 61 and 62 secured to the front and rear sides of the same which extend interiorly to the proximal extremity of the flexible elongate member 41.

A torquer 66 of the type described in U.S. Pat. No. 5,178,159 is mounted on the proximal extremity 42 of the flexible elongate member 41 for causing a rotation of a guide wire 21 when used in connection with catheterization procedures in a manner well known to those skilled in the art.

The proximal extremity 42 is also provided with a plurality of conducting sleeves (not shown) of the type disclosed in U.S. Pat. No. 5,178,159. In the present invention, one or more additional sleeves can be provided to make connection to the conductors hereinafter described. The proximal extremity 42 of the flexible elongate member is removably disposed within a housing 68 of the type described in U.S. Pat. Nos. 5,178,159, 5,348,481 and 5,358,409 that makes electrical contact with the sleeves on the proximal extremity 42 while permitting rotation of the sleeves and the flexible elongate member 41. The housing 68 carries female receptacles (not shown) which receive the sleeves and which are connected to a cable 71 connected to a connector 72. The connector 72 is connected to another mating connector 73 carried by the cable 26 and connected into the interface box 27.

The portion of the guide wire 21 therefore described is substantially conventional. In accordance with the present invention it is provided with a pressure measuring capability in the form of a pressure sensor assembly 76 which is mounted within the intermediate or transition housing 51. The pressure sensor assembly 76 consists of a diaphragm structure 77 supported by a base plate 78. The diaphragm structure 77 is formed of suitable materials such as "n" type or "p" type 100 oriented silicon with a resistivity of approximately 6-8 ohm-centimeters. The diaphragm structure 77 is a die made from such a wafer. In accordance with the present invention, the die has a suitable length, as for example, 1050 microns and for a 0.014" guide wire has a width of 250 microns and for a 0.018" guide wire has a width of between 250 and 350 microns. It can have a suitable thickness, as for example, 50 microns. A rectangular diaphragm 79 is formed in the diaphragm structure 77 of a suitable thickness, as for example, 2.5 microns and having dimensions such as a length of 350 microns. The diaphragm 79 has first and second or top and bottom surfaces 80 and 81. The diaphragm is formed by utilization of conventional masking and crystal etching techniques which create a die with two parallel sloping endwalls 82 and two parallel sidewalls 83 extending at right angles to the end walls 82 leading down to the top surface 80 of the diaphragm 79 to form a well 84. As hereinafter explained, the diaphragm 79 is made relatively wide in comparison to the diaphragm structure 77 so that what remains is a relatively narrow rim 86 formed by side portions 87 and 88 and an end portion 89. As can be seen from FIGS. 6, 7 and 8, the diaphragm 79 is located at or near one end of the diaphragm structure or die 77. It has been found that it is desirable to provide a rectangular geometry for the diaphragm 79 rather than a square geometry in order to obtain the highest possible sensitivity for pressure measurements. For example, it has been found that the rectangular diaphragm provides approximately 1.5 times more sensitivity than does a square diaphragm for the same diaphragm thickness and width.

In etching the well 84 to form the diaphragm 81, an impurity can be implanted into the backside of the diaphragm structure 77 before the etching process is commenced so that etching will stop at the desired depth, as for example, within 2 to 3 microns of the bottom surface 81 to provide a diaphragm 79 having a thickness ranging from 2 to 5 microns, and for example, the preferred thickness of 2.5 microns. Because the rim 86 provided on the diaphragm structure 77 surrounding the rectangular diaphragm 79 is relatively thin, the base plate 78 provides support for this rim to provide the necessary strength for the pressure sensor 76.

In order to obtain adequate performance characteristics such as sensitivity in the miniaturized pressure sensor assembly 76 hereinbefore described, it has been found desirable to have as much of the width of diaphragm structure 77 as possible be occupied by the diaphragm 79 and at the same time to minimize the portion of the diaphragm structure 77 occupied by the rim. In order to achieve a diaphragm width ratio of at least 0.45 to 0.9 with respect to the width of the diaphragm 79 to the width of the structure 77 and therefore to obtain the largest diaphragm possible in the diaphragm structure 77, diaphragm 79 is made relatively large compared to rim 86. With current manufacturing technology, it has been found feasible to have a width of rim 86 of 40 microns, which provides for a diaphragm 79 of 170 microns in a 250 micron-wide diaphragm structure 77 to provide a diaphragm width ratio of 0.68. In a larger diaphragm structure such as 350 microns wide, the pressure sensor assembly 76 can be made stronger by increasing the rim width to 90 microns. Alternatively, it can be made more sensitive by increasing the diaphragm width up to 270 microns. This results in a diaphragm width ratio for a 350 micron-wide device of between 0.49 and 0.77, depending on what combination of sensitivity and strength is desired.

Prior to or after the formation of the rectangular diaphragm 79, a plurality of V-shaped recesses or grooves 91 are formed in the diaphragm structure 77 on the end opposite the end at which the diaphragm 79 is located and on the side opposite the side in which the well 84 is formed. These V-shaped recesses 91 also can be formed in a conventional manner by the use of a conventional etch. It should be appreciated that if desired, the etching can be stopped so that the recesses formed are short of a complete V. By way of example, if the etching for the V-shaped recess was stopped at a depth of 12 microns, the bottom of the substantially V-shaped recess or trench 91 would be approximately 8 microns wide.

After the V-shaped or substantially V-shaped recesses have been formed, a P+ diffusion utilizing a suitable material such as boron can be carried out to create a V-shaped region 92 (in the structure 77) which underlies the V-shaped recess 91. Utilizing suitable masking a common layer 93 of a suitable material such as chromium is sputtered into the V-shaped recess 91 to a suitable thickness as for example, 300 Angstroms followed by a layer 94 of a suitable material such as gold of a suitable thickness as for example 3000 Angstroms. The layers 93 and 94 overlie the bottom surface 81 to form pads 96 thereon. In depositing the gold in the V-shaped recess 91 it is desirable to terminate the gold just short of the leftmost extremity of the V-shaped recess as viewed in FIG. 8 in order to minimize the likelihood of lead-to-lead shorting during the dicing operation when a wafer is sawed up into individual sensor chips.

By way of example, the spacing between V-grooves 91 from center to center can be 75 microns with the V-groove having a width of 25 microns and having a typical depth of 18 microns. The metal pads 96 formed by the chromium and gold layers 93 and 94 can have a suitable width as for example, 50 microns with the overlap on each side being approximately 12.5 microns to provide a spacing of approximately 25 microns between adjacent V-shaped pads 96. The bottom of the V-shaped groove can have a total length of approximately 250 microns.

The regions 92 formed from the P+ diffusion have patterns that extend to the right from the three V-shaped recesses 91 as viewed in FIG. 8 for a distance so that they underlie the approximate midpoint of the diaphragm 81 on opposite sides to provide generally U-shaped portions or resistors 92*a* which are located on the diaphragm in areas of a maximum stress to provide maximum sensitivity to pressure changes. The resistors 92*a* are provided with opposite ends, one end being connected to one each of the V-grooves and the other end being connected to the center or common V-groove. Contact is made to these P+ diffused regions by the chromium and gold layers 93 and 94 hereinbefore described.

The base plate 78 can be formed of a suitable material such as Pyrex supplied by Corning Glassworks and can have the same width as the diaphragm structure 77 but has a length which is less than the length of the diaphragm structure 77 so that the V-shaped grooves 91 are exposed on the underside of the diaphragm structure 77 as shown in FIG. 6. It also can have a suitable length such as 850 microns. It is provided with a rectangular recess or cavity 101 having substantially the same size as the diaphragm 79. It can be etched into the Pyrex by suitable means such as a conventional etching process utilizing hydrochloric acid. After the etching has been completed to form the rectangular recess 101 it is bonded to the lower surface of the diaphragm structure 77 to form a hermetic seal with respect to the same so that the cavity 101 underlies the diaphragm 79 and is exposed to the bottom surface 81 of the diaphragm 79. The cavity 101 below the diaphragm 79 serves as a reference pressure chamber and can be filled with a suitable fluid. For example, it can be filled with air to half an atmosphere to provide a partial vacuum. Alternatively, the cavity 101 can be filled to one atmosphere or it can be completely evacuated.

A trifilar lead structure 106 is connected to the rectangular diaphragm structure 77. It has insulated copper leads 107 of a suitable diameter as for example 48AWG soldered into place to the V-shaped recesses 91 so that the leads 107 extend outwardly therefrom and lie in a plane parallel to the plane of the diaphragm structure 77. The trifilar lead construction 106 provides insulation around each lead and in addition there is provided additional insulation which surrounds the leads and which interconnects the leads into a single unit which can be readily extended through the hypotube forming the flexible elongate member 41.

The pressure sensor assembly 76 is mounted within a cutout 111 provided in the transition housing 51 and secured therein by suitable means such as an epoxy 112 so that the outer surface of the pressure sensor assembly 76 is generally flush with the outer surface of the transition housing 51 (see FIG. 3) and so that the diaphragm 79 is exposed to ambient and the leads 106 extend through the flexible elongate member 41 to the proximal extremity 42 of the same where they are connected to the sleeves (not shown) carried by the proximal extremity 42 disposed within the housing 68. Also, the conductors 61 and 62 of the velocity sensing transducer 58 are connected to two of such sleeves (not shown) provided on the proximal extremity 42.

A schematic of the wiring for the pressure sensor assembly 76 is shown in FIG. 12. The two generally U-shaped portions 92a on opposite sides of the diaphragm 79 are represented as resistors and are connected to the three leads 107 in the manner shown. One of the first of the outside leads 107 is "SIGNAL OUT" (+) and the second or other outside lead is "SIGNAL OUT" (−) and the third or middle lead is a common lead as shown. This pattern makes it possible to not cross leads and has the third lead going up the middle or center of the die or the diaphragm structure 77. It can be seen that the two resistors 92a connected as shown form a half bridge one of the resistors responds positively to pressure change and the other resistor responds negatively to a pressure change. Thus, as a pressure is supplied to the diaphragm 79, one resistor increases in value and the other resistor decreases in value to provide a voltage change. By applying the same current to both resistors at the same time, temperature effects can be measured because temperature change will affect both of the resistors in the same way so that the pressure measurements can be compensated for any changes in temperature which are sensed by the resistors 92a. The changes in resistivity caused by the temperature changes in the resistors will cancel each other out because of the half bridge configuration used. In connection with FIG. 12 it can be seen that with the use of three leads it is possible to obtain temperature compensation by utilizing a half-bridge configuration for the pressure sensor. Alternatively, a more precise temperature compensation can be provided by directly measuring the two resistances, and then solving the mathematical equations which relate temperature and pressure to the two sensor resistances.

Operation and use of the guide wire 21 in performing a catheterization procedure such as angioplasty may now be briefly described as follows: Let it be assumed that a guiding catheter (not shown) has been introduced into the femoral artery of the patient 22 shown in FIG. 1 with the distal extremity near the desired location in the heart in which it is desired to perform an angioplasty. The guide wire 21 of the present invention is inserted into the guiding catheter. At the time that its distal extremity is in close proximity to the distal extremity of the guiding catheter, the pressure output signal from the guide wire is compared with that of the guiding catheter assuming that the guide wire is provided with pressure sensing capabilities. If there is a difference between the two pressure measurements, the pressure measurement from the guide wire 21 is equalized with that from the guiding catheter at the control console 29. The distal extremity of the guide wire 21 is then advanced so that it is proximal of the stenosis to be treated at which time a pressure measurement is made. After this pressure measurement has been recorded, the distal extremity of the guide wire is then advanced through the stenosis and another pressure measurement made to determine whether the stenosis is severe enough to require treatment by angioplasty. Alternatively, the distal extremity of guide wire 21 can be immediately advanced to the distal side of the stenosis rather than making a pressure measurement proximal of the stenosis and thereafter comparing the pressure measurement on the distal extremity being measured by the guide wire 21 with the pressure measurement being provided proximal of the stenosis by the guiding catheter. If it is determined that the stenosis causes a partial occlusion which is severe enough to warrant use of an angioplasty procedure, an angioplasty catheter having a balloon thereon (not shown) can be advanced over the guide wire 21 and advanced into the stenosis to dilate the stenosis. After dilation has occurred, the angioplasty balloon can be withdrawn from the stenosis and pressure measurements can be made proximal and distal of the stenosis to ascertain the effect of the angioplastic treatment. If the pressure measurements indicate that the original dilation by the angioplasty balloon has been inadequate, another balloon catheter as for example, one having a balloon of a greater diameter can then be positioned over the guide wire 21 by utilizing an exchange wire if appropriate. The larger angioplasty catheter can be advanced through the stenosis and inflated to again dilate the stenosis to a larger size after which it can be withdrawn. Thereafter, pressure measurements proximal and distal of the stenosis can again be made to ascertain whether or not the second dilation which has been performed is adequate. The decisions to be made in connection with such procedures can be readily made by use of the control console 29 by observing the traces 33 and 34 on the video monitor 31.

It also should be appreciated that at the same time Doppler velocity measurements can be made by the transducer 58. That information can be used in connection with the pressure measurements to ascertain the need for performing the angioplasty procedure or for determining the efficacy of the angioplasty procedure performed. Because of the very small diameters of the guide wires as for example, 0.018" or 0.014", it is possible to utilize the guide wire 21 of the present invention with very small coronary vessels in the heart. In connection with the leads from the Doppler transducer 58 it should be appreciated that if desired some of the conductors provided for the Doppler ultrasound transducer can be shared with the wires or conductors provided for the pressure sensor assembly 76. Thus, two of the wires for the pressure sensor can be utilized for the Doppler transducer because the pressure sensor operates at DC or up to a few hundred Hz or KHz whereas the Doppler sensor operates at 10 MHz and above. These frequency ranges can be readily separated by one skilled in the art by using simple filters and the appropriate circuitry.

In connection with the present invention it should be appreciated that rather than bonding the leads 107 into the V-grooves or V-shaped recesses 91, the Pyrex base plate 78 can be formed so it has the same length as the diaphragm structure 77. V-shaped or U-shaped grooves can be formed in the base plate underlying the V-shaped grooves to in effect form little tunnels which can be utilized for receiving the wires 107 and for them to be soldered therein. Such a construction aids in the placement of wires which are of the very small diameter, as for example, 1 mil.

Another embodiment of a guide wire 121 incorporating the present invention is shown in FIG. 13. In the guide wire 121, pressure sensor assembly 76 is mounted in a tip housing 122. The tip housing 122 can be substituted at the end cap 57 and threaded into the distal extremity 56 of the coil 54. The tip housing 122 can be formed of a suitable material such as stainless steel having an outside diameter of 0.018" and a wall thickness of 0.001" to 0.002". The sensor assembly 76 can be of the type hereinbefore described and can be mounted in a cutout 123 provided in the tip housing 122 much in the same manner as the sensor assembly 76 was mounted in the cutout 111 in the transition housing 51 such as by use of an epoxy 124. An hemispherical end cap 126 formed of a radiopaque material such as palladium or tungsten platinum alloy can be mounted on the distal extremity of the tip housing 122. Alternatively, the end cap 126 can be formed of a non-radiopaque material such as epoxy or silicone rubber.

Thus it can be seen with the embodiment of the guide wire 121 shown in FIG. 13, the guide wire 121 can be utilized in the same manner as the guide wire 21 hereinbefore described with the exception of it cannot be used for making velocity measurements because that capability has been removed from the guide wire 121.

Another guide wire 131 incorporating the present invention is shown in FIG. 14 in which two pressure sensors 76 have been provided. The sensors 76 have been spaced apart a suitable distance as for example, 3 centimeters with one of the pressure sensors being mounted in the transition housing 51 and the other pressure sensor being mounted in a tip housing 122 of the type shown in FIG. 13. With such an arrangement, it can be seen that the distal extremity of the guide wire 131 can be advanced across a stenosis in a vessel with the pressure sensor 76 mounted in the tip housing being distal of the stenosis to measure distal pressure and the pressure sensor 76 in the transition housing 51 being proximal of the stenosis to measure proximal pressure. Thus, it can be seen that it is possible to measure simultaneously the distal pressure and the proximal pressure with respect to a stenosis in a vessel. This may give more accurate measurements than utilizing the proximal pressure being sensed by the guiding catheter.

When using two pressure sensors 76 in the same guide wire as shown in FIG. 14, it is possible to utilize the same common wire for both of the transducers, thus making it necessary to provide only five wires rather than six wires for the two pressure sensors.

Still another guide wire 141 incorporating the present invention is shown in FIG. 15 in which a cover 142 is provided for covering the pressure sensor assembly 76 provided in the transition housing 51. The cover is elongate and extends the length of the cutout 111 and is arcuate in cross-section so that it conforms to the conformation of the transition housing 51. The cover 142 can be secured in place by a suitable means such as an adhesive. The cover 142 overlying the pressure sensor assembly 76 is provided with a pin hole 143 which immediately overlies the diaphragm 79. The pin hole 143 can be of a suitable size as for example 2-5 mils in and preferably 3 mils in diameter. The cover 142 serves to prevent the large opening provided by the cutout 111 from collecting blood which could possibly clot. The cover 142 also serves to protect the sensor 76 from damage. It also prevents the sensor 76 from being broken loose during use of the guide wire 141. It should be appreciated that if desired, the volume beneath the cover 142 can be filled with viscous fluid such as oil which can be utilized for transmitting pressure from the pin hole 143 to the diaphragm 81. With a small size pin hole 143, the viscous fluid provided would not have a tendency to bleed out of the transition housing 51. The viscous fluid would be held in place because of the surface tension of the fluid. Because there is a very short distance between the pin hole 143 and the diaphragm 79, there would be very little tendency for the viscous fluid to damp any pressure signal transmitted from the blood in which the guide wire 141 is disposed to the diaphragm.

Another guide wire 151 incorporating the present invention is shown in FIG. 16 having a transition housing 152 formed of a suitable material such as stainless steel and having an OD of 0.018" or less. A pressure sensor assembly 76 of the type hereinbefore described is mounted within the bore 153 of the transition housing 152 and is secured therein by mounting the same in an epoxy 154 while leaving the area immediately above the diaphragm 79 exposed to a pin hole 156 provided in the transition housing 152. The space overlying the diaphragm 81 exposed to the pin hole 156 can be filled with a viscous fluid 157 such as oil. The viscous fluid 157 can be retained within the desired location by a barrier 158 formed on the proximal side of the pressure sensor 76 having the trifilar lead structure 106 extending therethrough, in sealing engagement therewith. To seal the other end of the bore 153, an intermediate end cap 161 can be provided which is provided with a barrier 182 extending thereacross to seal the bore 153. The intermediate end cap 161 can be bonded to the transition housing 152 by a suitable means such as an adhesive (not shown). The coil 54 can be threaded onto the intermediate end cap 161 and can be threaded onto a tip housing 166 that carries a rounded hemispherical tip 167. With such a construction it can be seen that the pressure sensor assembly 76 is protected within the transition housing 152.

In FIG. 16A a guide wire 168 is shown which is very similar to the guide wire 151 with the exception that the housing 152 has been provided on the distal extremity of the coil 46 with the tip 167 directly mounted on the housing 152 for closing the bore 153.

In FIG. 17 there is shown another embodiment of a guide wire 171 incorporating the present invention which has an integral balloon carried thereby. A guide wire with an integral balloon is described in U.S. Pat. No. 5,226,421. The guide wire 171 consists of a flexible elongate tubular member 173 in a manner formed of a suitable material such as plastic which is provided with a distal extremity 174. An inflatable balloon 176 is secured to the distal extremity 174 of the flexible elongate member 173 in a manner well known to those skilled in the art. Such a balloon can be formed integral with the distal extremity and can be formed of the same material as the flexible elongate tubular member 173. Alternatively, it can be formed of a different material or the same material and be formed as a separate part and secured to the distal extremity 174 by suitable means such as adhesive.

The balloon 176 is provided with a distal extremity which is closed and which is secured to the proximal extremity of a coil spring 178 formed of a radiopaque material such as a palladium or tungsten platinum alloy threaded onto a tip housing 179. The tip housing 179 can be formed in a manner similar to the tip housing 122 shown in FIG. 13 having a pressure sensor 76 mounted therein and carrying an end cap 181. The trifilar leads 106 connected to the sensor 76 extend through the coil 118 and through the balloon 176 and through the flexible elongate tubular member 172 to the proximal extremity thereof. A core wire 186 formed of a suitable material such as stainless steel is provided in the flexible elongate member 173 and can be provided with a diameter such as disclosed in U.S. Pat. No. 5,226,421. The core wire 186 is provided with a tapered portion 186a extending through the balloon which has a distal extremity secured to the housing 179 by a suitable means such as the epoxy utilized for mounting the sensor 76 within the housing. The flexible elongate tubular member 172 is provided with a balloon inflation lumen 187 which can be used for inflating and deflating the balloon 176.

The guide wire 171 with an integral balloon 171 can be utilized in a manner similar to that hereinbefore described for the other guide wires. Rather than deploying a separate catheter with a balloon thereon over the guide wire, the guide wire 171 itself carries the balloon 176 which can be inflated to dilate the stenosis after the proximal and distal pressure measurements have been made by the tip mounted sensor 76. After the balloon 176 has been deflated, the pressure measurement can be made to ascertain the pressure in the distal extremity after dilation has occurred. If necessary, the balloon 176 can be re-inflated to perform another dilation of the stenosis to obtain improved blood flow through the stenosis.

After an appropriate dilation has occurred, the guide wire 171 with integral balloon can be removed in a conventional manner. The angioplasty procedure can then be completed in a conventional manner.

From the foregoing, it can be seen that there has been provided an ultra miniature pressure sensor which can be utilized on guide wires having a diameter of 0.018" and less which can be utilized for making accurate measurements proximal and distal of a stenosis in the coronary vessel. This is made possible because of the small size of the pressure sensor incorporated into the distal extremity of the guide wire. In addition to sensing pressure, flow velocity can also be obtained by the use of a distally mounted velocity transducer provided on the same guide wire as on which the pressure sensor is mounted. Alternatively, additional first and second pressure sensors can be provided on the distal extremity of a guide wire so that pressure measurements can be made simultaneously, proximally and distally of the stenosis. The pressure sensor is constructed in such a manner so that it can be readily incorporated within the confines of a small guide wire as for example, 0.018" and less. It can be constructed to avoid a large opening in the distal extremity of the guide wire to inhibit or prevent the formation of clots. The pressure sensor also can be protected so that it cannot be readily damaged or broken loose. In addition, where desired, the guide wire can be provided with an integrally mounted balloon on its distal extremity so that the guide wire can be utilized for performing an angioplasty procedure while at the same time facilitating the making of pressure measurements, proximal and distal of the stenosis being treated.

The invention claimed is:

1. A pressure sensor apparatus, comprising:
    a long proximal hypotube having an outside diameter of 0.018" or less,
    a flexible floppy tip extending distal of the long proximal hypotube, the flexible floppy tip comprising:
        a first flexible element, disposed near a distal portion of the long proximal hypotube, with an outer diameter of 0.018" or less and an increased flexibility relative to the long proximal hypotube;
        a short hypotube sensor housing disposed near a distal extremity of the first flexible element, the sensor housing having:
            a cylindrical external wall having an outer diameter of 0.018" or less,
            a length between 1 mm and 5 mm,
            a lumen, and
            a cutout in the cylindrical external wall;
        a second flexible element, disposed near a distal extremity of the short hypotube sensor housing, with an outer diameter of 0.018" or less and an increased flexibility relative to the long proximal hypotube; and
        a solid state pressure sensor mounted within the short hypotube sensor housing, such that:
            a pressure sensitive region located at or near one end of the solid state pressure sensor projects into the lumen of the short hypotube sensor housing without contacting the cylindrical external wall of the sensor housing; and
            the pressure sensitive region is exposed to ambient by the cutout in the cylindrical external wall of the sensor housing,
            wherein the pressure sensitive region includes a diaphragm structure, a base plate, and at least one resistive element responsive to changes in pressure; and
        three electrical conductors extending from a proximal portion of the long proximal hypotube to the solid state pressure sensor, the three electrical conductors coupled to the solid state pressure sensor such that the coupled portions of the three electrical conductors and the solid state pressure sensor are positioned within the short hypotube sensor housing.

2. The pressure sensor apparatus of claim 1, wherein the at least one resistive element consists of two resistive elements.

3. The pressure sensor apparatus of claim 2, wherein at least one of the two resistive elements is disposed on the solid state pressure sensor in the pressure sensitive region.

4. The pressure sensor apparatus of claim 1, wherein the solid state pressure sensor comprises a semiconductor material.

5. The pressure sensor apparatus of claim 1, wherein at least one resistive element overlies at least a portion of the diaphragm.

6. The pressure sensor apparatus of claim 1, comprising an end cap disposed distally from the second flexible element.

7. The pressure sensor apparatus of claim 6, wherein the end cap is rounded.

8. The pressure sensor apparatus of claim 7, wherein the end cap is hemi-spherical.

9. The pressure sensor apparatus of claim 1, wherein the three electrical conductors comprise a trifilar structure.

10. The pressure sensor apparatus of claim 1, comprising a core wire extending from a proximal extremity of the long proximal hypotube, through the sensor housing, and to a distal extremity of the second flexible element.

11. The pressure sensor apparatus of claim 1, wherein the second flexible element is a coil and comprises a radiopaque material.

12. The pressure sensor apparatus of claim 1, wherein the at least one resistive element comprises a first resistive element that responds positively to a pressure change and a second resistive element that responds negatively to the pressure change and the first and second resistive elements form a half bridge.

13. The pressure sensor apparatus of claim 1, wherein the base plate has a rectangular profile.

14. The pressure sensor apparatus of claim 1, wherein the diaphragm is positioned directly opposite the cutout in the sensor housing within the lumen of the sensor housing.

15. The pressure sensor apparatus of claim 1, wherein the first flexible element comprises a flexible elongate tubular member formed of a plastic material.

16. The pressure sensor apparatus of claim 1, wherein the first flexible element is a hypotube formed of a plastic material.

17. The pressure sensor apparatus of claim 1, wherein the first flexible element is a coil.

18. The pressure sensor apparatus of claim 1, wherein the first flexible element comprises a balloon.

19. The pressure sensor apparatus of claim 1, further comprising a core wire extending along a length of the long proximal hypotube and within the first flexible element.

20. The pressure sensor apparatus of claim 19, wherein the core wire tapers within the first flexible element.

21. The pressure sensor apparatus of claim 20, wherein the core wire tapers from a larger diameter to a smaller diameter as the core wire extends distally within the first flexible element.

22. The pressure sensor apparatus of claim 21, wherein the first flexible element comprises a plastic material.

23. The pressure sensor apparatus of claim 19, wherein the first flexible element has a length of approximately 27 cm.

24. The pressure sensor apparatus of claim 23, wherein the second flexible element is a coil and has a length of approximately 3 cm.

25. The pressure sensor apparatus of claim 1, wherein the first flexible element comprises a plastic material.

26. The pressure sensor apparatus of claim 1, wherein the solid state pressure sensor is secured to the sensor housing by an adhesive.

27. The pressure sensor apparatus of claim 1, wherein one of the three electrical conductors provides a common lead to the solid state pressure sensor.

28. The pressure sensor apparatus of claim 27, wherein two of the three electrical conductors are return leads from the solid state pressure sensor.

29. The pressure sensor apparatus of claim 28, wherein the common conductor is coupled to a pair of resistive elements and the return conductors are each coupled to a single one of the pair of resistive elements.

30. A pressure sensor apparatus, comprising:
a long proximal hypotube having an outside diameter of 0.018" or less,
a flexible floppy tip extending distal of the long proximal hypotube, the flexible floppy tip comprising:
a short hypotube sensor housing disposed distal of a distal extremity of the long proximal hypotube, the short hypotube pressure sensor housing having;
an outer diameter of 0.018" or less;
a length between 1 mm and 5 mm, and
a cutout in a wall thereof;
a first flexible element, disposed between the long proximal hypotube and the short hypotube sensor housing, with an outer diameter of 0.018" or less and an increased flexibility relative to the long proximal hypotube;
a second flexible element, disposed distal of the short hypotube sensor housing, with an outer diameter of 0.018" or less and an increased flexibility relative to the long proximal hypotube;
a solid state pressure sensor comprising a pressure sensitive region located at or near one end thereof with a diaphragm and at least one resistive element responsive to pressure;
wherein the solid state pressure sensor is disposed within the short hypotube sensor housing such that:
the pressure sensitive region is spaced from an external wall of the short hypotube sensor housing; and
the diaphragm is exposed to ambient by the cutout in the short hypotube sensing housing; and
three electrical conductors extending from a proximal extremity of the long proximal hypotube to the solid state pressure sensor, a distal portion of the electrical conductors coupled to the solid state pressure sensor within the short hypotube sensor housing.

31. The pressure sensor apparatus of claim 30, wherein the second flexible element is a coil and comprises a radiopaque material.

32. The pressure sensor apparatus of claim 30, wherein the long proximal hypotube has an outside diameter of approximately 0.014" or less.

33. The pressure sensor apparatus of claim 30, wherein the outer diameter of the sensor housing is equal to the outer diameter of the long proximal hypotube.

34. The pressure sensor apparatus of claim 30, further comprising a core wire extending along a length of the long proximal hypotube.

35. The pressure sensor apparatus of claim 30, wherein the first flexible element comprises a flexible elongate tubular member formed of a plastic material.

36. The pressure sensor apparatus of claim 30, wherein the first flexible element is a hypotube formed of a plastic material.

37. The pressure sensor apparatus of claim 30, wherein the first flexible element is a coil.

38. The pressure sensor apparatus of claim 30, wherein the first flexible element comprises a balloon.

39. The pressure sensor apparatus of claim 30, further comprising a core wire extending along a length of the guidewire and within the first flexible element.

40. The pressure sensor apparatus of claim 39, wherein the core wire tapers within the first flexible element.

41. The pressure sensor apparatus of claim 40, wherein the core wire tapers from a larger diameter to a smaller diameter as the core wire extends distally within the first flexible element.

42. The pressure sensor apparatus of claim 39, wherein the first flexible element has a length of approximately 27 cm.

43. The pressure sensor apparatus of claim 42, wherein the second flexible element is a coil and has a length of approximately 3 cm.

44. The pressure sensor apparatus of claim 43, wherein the sensor housing has a length between 1 mm and 5 mm.

45. The pressure sensor apparatus of claim 30, wherein the first flexible element comprises a plastic material.

46. The pressure sensor apparatus of claim 30, further comprising an end cap disposed distally from the second flexible element.

47. The pressure sensor apparatus of claim 46, wherein the end cap is rounded.

48. The pressure sensor apparatus of claim 47, wherein the end cap is hemi-spherical.

49. The pressure sensor apparatus of claim 30, wherein the solid state pressure sensor is secured to the sensor housing by an adhesive.

50. The pressure sensor apparatus of claim 30, wherein one of the three conductors provides a common conductor to the solid state pressure sensor.

51. The pressure sensor apparatus of claim 50, wherein two of the three conductors are return conductors from the solid state pressure sensor.

52. The pressure sensor apparatus of claim 51, wherein the common conductor is coupled to a pair of resistive elements and the return conductors are each coupled to a single one of the pair of resistive elements.

53. A pressure sensor apparatus comprising:
a long proximal hypotube having an outside diameter of 0.018" or less,
a first flexible element, disposed distal of the long proximal hypotube, with an outer diameter of 0.018" or less and an increased flexibility relative to the long proximal hypotube,
a short hypotube sensor housing disposed distal of a distal extremity of the first flexible element, and having a cylindrical wall with an outer diameter of 0.018" or less, a length between 1 mm and 5 mm, and a cutout in the cylindrical wall;

a second flexible element, disposed distally from the short hypotube sensor housing, with an outer diameter of 0.018" or less and an increased flexibility relative to the long proximal hypotube, a solid state pressure sensor mounted within the short hypotube sensor housing such that a pressure sensitive region of the solid state pressure sensor is exposed to ambient via the cutout, the solid state pressure sensor comprising at least one resistive element responsive to pressure, and electrical conductors extending from a proximal extremity of the long proximal hypotube to the solid state pressure sensor, wherein the electrical conductors are coupled to the solid state pressure sensor within the short hypotube sensor housing and wherein the electrical conductors are coupled to conducting sleeves at the proximal extremity of the long proximal hypotube.

54. The pressure sensor apparatus of claim 53, wherein the electrical conductors comprise three conductors.

55. The pressure sensor apparatus of claim 53, wherein the second flexible element is a coil and comprises a radiopaque material.

56. The pressure sensor apparatus of claim 53, wherein the at least one resistive element comprises a first resistive element that responds positively to a pressure change and a second resistive element that responds negatively to the pressure change and the first and second resistive elements form a half bridge.

57. The pressure sensor apparatus of claim 56, wherein at least one of the plurality of resistive elements is disposed on the solid state pressure sensor in the pressure sensitive region.

58. The pressure sensor apparatus of claim 53, wherein the first flexible element comprises a flexible elongate tubular member formed of a plastic material.

59. The pressure sensor apparatus of claim 53, wherein the first flexible element is a hypotube formed of a plastic material.

60. The pressure sensor apparatus of claim 53, wherein the first flexible element is a coil.

61. The pressure sensor apparatus of claim 53, wherein the first flexible element is a balloon.

62. The pressure sensor apparatus of claim 53, further comprising a core wire extending along a length of the long proximal hypotube and within the first flexible element.

63. The pressure sensor apparatus of claim 53, wherein the core wire tapers within the first flexible element.

64. The pressure sensor apparatus of claim 63, wherein the core wire tapers from a larger diameter to a smaller diameter as the core wire extends distally within the first flexible element.

65. The pressure sensor apparatus of claim 53, wherein the first flexible element has a length of approximately 27 cm.

66. The pressure sensor apparatus of claim 65, wherein the second flexible element is a coil and has a length of approximately 3 cm.

67. The pressure sensor apparatus of claim 66, wherein the sensor housing has a length between 1 mm and 5 mm.

68. The pressure sensor apparatus of claim 53, wherein the flexible element comprises a plastic material.

69. The pressure sensor apparatus of claim 53, further comprising an end cap disposed distally from the the second flexible element.

70. The pressure sensor apparatus of claim 69, wherein the end cap is rounded.

71. The pressure sensor apparatus of claim 70, wherein the end cap is hemi-spherical.

72. The pressure sensor apparatus of claim 53, wherein at least a portion of the solid state pressure sensor is secured to the sensor housing by an adhesive.

73. The pressure sensor apparatus of claim 53, wherein one of three electrical conductors provides a common lead to the solid state pressure sensor.

74. The pressure sensor apparatus of claim 73, wherein two of the three electrical conductors are return leads from the solid state pressure sensor.

75. The pressure sensor apparatus of claim 74, wherein the common lead is coupled to a pair of resistive elements and the return leads are each coupled to a single one of the pair of resistive elements.

* * * * *